United States Patent [19]

Heeres et al.

[11] Patent Number: 5,707,977
[45] Date of Patent: Jan. 13, 1998

[54] WATERSOLUBLE AZOLE ANTIFUNGALS

[75] Inventors: Jan Heeres, Vosselaar; Leo Jacobus Jozef Backx, Arendonk; Luc Alfons Leo Van der Eycken, Vosselaar; Frank Christopher Odds, Schilde; Jean Louis Mesens, Wechelderzande, all of Belgium

[73] Assignee: Janssen Pharmaceutica, N.V., Beerse, Belgium

[21] Appl. No.: 666,270

[22] PCT Filed: Jan. 17, 1995

[86] PCT No.: PCT/EP95/00174

§ 371 Date: Jun. 20, 1996

§ 102(e) Date: Jun. 20, 1996

[87] PCT Pub. No.: WO95/19983

PCT Pub. Date: Jul. 27, 1995

Related U.S. Application Data

[63] Continuation-in-part of Ser. No. 185,352, Jan. 24, 1994, abandoned.

[51] Int. Cl.⁶ ............ A61K 31/495; A61K 31/675; C07D 405/14; C07F 9/6558
[52] U.S. Cl. ............ 514/85; 514/236.2; 514/252; 544/121; 544/357; 544/337; 544/364; 544/366; 544/370
[58] Field of Search .......... 544/121, 337, 544/357, 364, 366, 370; 514/85, 236.2, 252

[56] References Cited

U.S. PATENT DOCUMENTS

| | | | |
|---|---|---|---|
| 4,267,179 | 5/1981 | Heeres et al. | 544/366 |
| 4,791,111 | 12/1988 | Heeres et al. | 514/252 |
| 5,039,676 | 8/1991 | Saksena et al. | 514/254 |

FOREIGN PATENT DOCUMENTS

| | | |
|---|---|---|
| 228125 | 7/1987 | European Pat. Off. |
| 283992 | 9/1988 | European Pat. Off. |
| 539938 | 5/1993 | European Pat. Off. |
| 9517407 | 6/1995 | WIPO |

*Primary Examiner*—Emily Bernhardt
*Attorney, Agent, or Firm*—Charles J. Metz

[57] ABSTRACT

A compound of formula (I),

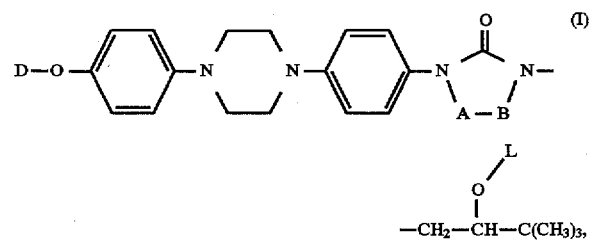

an acid or base addition salt thereof or a stereochemically isomeric form thereof, wherein A and B taken together form $-N=CH-$, $-CH=N-$, $-CH_2-CH_2$, $CH=CH-$, $-C(=O)-CH_2-$, $-CH_2-C(=O)$; D is a radical of formula

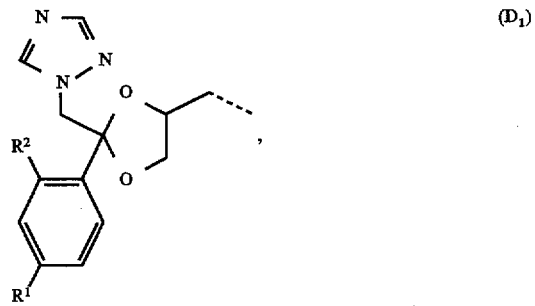

(D₁)

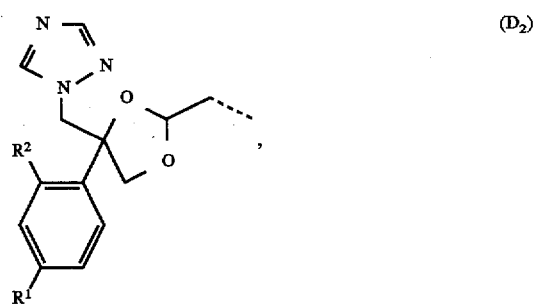

(D₂)

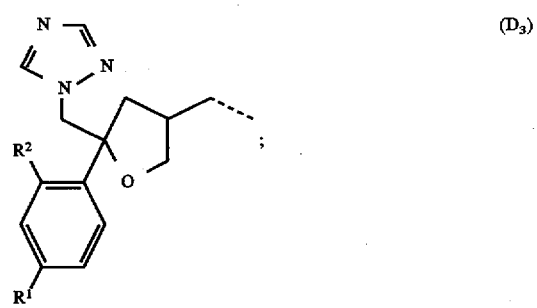

(D₃)

L is a radical of formula

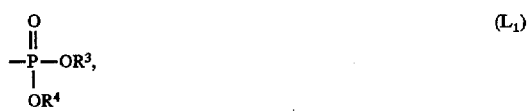

(L₁)

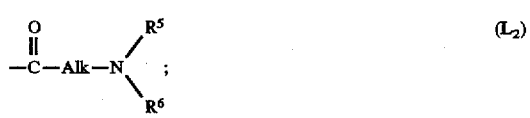

(L₂)

Alk is a $C_{1-4}$alkanediyl radical; $R^1$ is halo; $R^2$ is hydrogen or halo; $R^3$ is hydrogen, $C_{1-6}$alkyl, phenyl or halophenyl; $R^4$ is hydrogen, $C_{1-6}$alkyl, phenyl or halophenyl; $R^5$ is hydrogen or $C_{1-6}$alkyl; $R^6$ is hydrogen, $C_{1-6}$alkyl, $C_{1-6}$alkyloxycarbonyl, or $R^5$ and $R^6$ taken together with the nitrogen atom to which they are attached form a heterocyclic ring. Active intermediates, compositions and methods of preparing compounds, compositions are described.

12 Claims, No Drawings

WATERSOLUBLE AZOLE ANTIFUNGALS

CROSS-REFERENCE TO RELATED APPLICATIONS

This application is based upon PCT Application Ser. No. PCT/EP 95/00174, filed Jan. 17, 1995, which is a continuation-in-part of U.S. patent application Ser. No. 08/185,352, filed on Jan. 24, 1994, now abandoned.

The present invention is concerned with novel water-soluble broad-spectrum azole antifungals as well as the antifungally active precursors thereof.

Systemic fungal infections in man are relatively rare in temperate countries and many of the fungi that can become pathogenic normally live commensally in the body or are common in the environment. However, the past few decades have witnessed an increasing incidence of numerous life-threatening systemic fungal infections world-wide and these now represent a major threat to many susceptible patients, particularly those already hospitalized. Most of the increase can be attributed to improved survival of immunocompromised patients and the chronic use of antimicrobial agents. Moreover, the flora typical of many common fungal infections is also changing and this is presenting an epidemiological challenge of increasing importance. Patients at greatest risk include those with impaired immune functioning, either directly as a result of immunosuppression from cytotoxic drugs or HIV infection, or secondary to other debilitating diseases such as cancer, acute leukaemia, invasive surgical techniques or prolonged exposure to anti-microbial agents. The most common systemic fungal infections in man are candidosis, aspergillosis, histoplasmosis, coccidioidomycosis, paracoccidioidomycosis, blastomycosis and cryptococcosis.

Antifungals such as ketoconazole, itraconazole and fluconazole are being increasingly employed for the treatment and prophylaxis of systemic fungal infections in immunocompromised patients. However, concern about fungal resistance to some of these agents, especially the more narrow spectrum ones, e.g. fluconazole, is growing. Worse still, it is recognized in the medical world that about 40% of the people suffering from severe systemic fungal infections are hardly able, or not at all to receive medication via oral administration. This inability is due to the fact that such patients are in coma or suffer from severe gastroparesis. Hence the use of insoluble or sparingly soluble antifungals such as itraconazole or saperconazole, that are difficult to administer intravenously, is heavily impeded.

Consequently, there is a need for new antifungals, preferably broad-spectrum antifungals, against which there is no existing resistance and which can be administered intravenously. Preferably the antifungal should also be available in a pharmaceutical composition suitable for oral administration. This enables the physician to continue treatment with the same drug after the patient has recovered from his condition which required intravenous administration of said drug.

U.S. Pat. No. 4,267,179 discloses heterocyclic derivatives of (4-phenylpiperazin-1-yl-aryloxymethyl-1,3-dioxolan-2-yl)-methyl-1H-imidazoles and 1H-1,2,4-triazoles useful as antifungal and antibacterial agents. Said patent encompasses itraconazole, which is now available as a broad-spectrum antifungal on a world-wide basis.

U.S. Pat. No. 4,916,134 teaches novel 4-[4-[4-[[2-(2,4-difluorophenyl)-2-(1H-azolylmethyl)-1,3-dioxolan-4-yl]methoxy]phenyl]-1-piperazinyl]phenyl]triazolones having improved antimicrobial properties. Said patent encompasses saperconazole.

U.S. Pat. No. 4,791,111 discloses derivatives of [[4-[4-(4-phenyl-1-piperazinyl)phenoxymethyl]-1,3-dioxolan-2-yl]methyl]-1H-imidazoles and 1H-1,2,4-triazoles, structurally related to some of the compounds of the present invention, which are taught to have favourable antimicrobial properties.

U.S. Pat. No. 5,039,676 discloses azole-methyl substituted tetrahydrofurans, structurally related to some of the compounds of the present invention, which are taught to have antifungal activity and EP-0,539,938 teaches analogous trisubstituted tetrahydrofuran antifungals.

The present invention concerns novel compounds of formula

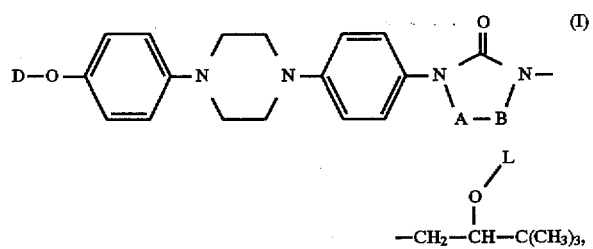

the pharmaceutically acceptable acid or base addition salts thereof and the stereochemically isomeric forms thereof, wherein A and B taken together form a bivalent radical of formula:
—N=CH— (a),
—CH=N— (b),
—CH$_2$—CH$_2$— (c),
—CH=CH— (d),
—C(=O)—CH$_2$— (e),
—CH$_2$—C(=O)— (f), wherein one hydrogen atom in the radicals (a) and (b) may be replaced with a $C_{1-6}$-alkyl-radical and up to two hydrogen atoms in radical (c), (d), (e) or (f) may be replaced by a $C_{1-6}$-alkyl-radical;

D is a radical of formula

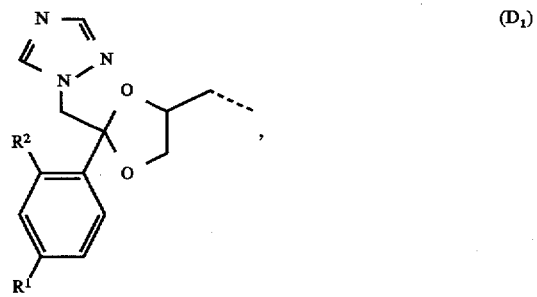

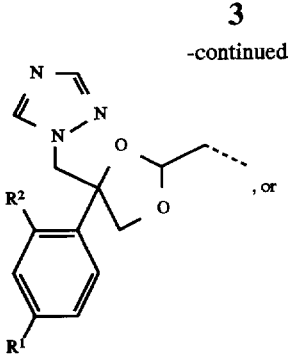
(D₂)

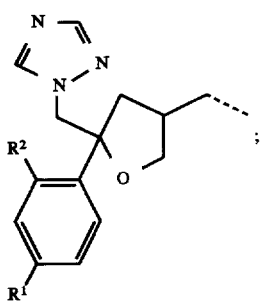
(D₃)

L is a radical of formula

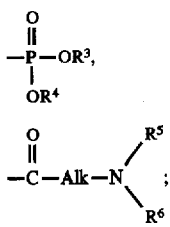
(L₁) or $$-\overset{O}{\underset{|}{\underset{R^6}{\overset{\|}{C}}}}-Alk-N\overset{R^5}{\underset{R^6}{\diagdown}}\ ;$$ (L₂)

Alk is a $C_{1-4}$alkanediyl radical;
$R^1$ is halo;
$R^2$ is hydrogen or halo;
$R^3$ is hydrogen, $C_{1-6}$alkyl, phenyl or halophenyl;
$R^4$ is hydrogen, $C_{1-6}$alkyl, phenyl or halophenyl;
$R^5$ is hydrogen or $C_{1-6}$alkyl;
$R^6$ is hydrogen, $C_{1-6}$alkyl, $C_{1-6}$alkyloxycarbonyl, or
$R^5$ and $R^6$ taken together with the nitrogen atom to which they are attached form a pyrrolidine, piperidine, morpholine, piperazine or substituted piperazine ring, said substituted piperazine being a piperazine ring substituted on the 4-position of the piperazine ring with $C_{1-6}$alkyl, hydroxy$C_{1-6}$alkyl, amino$C_{1-6}$alkyl, mono- or di($C_{1-6}$alkyl)amino$C_{1-6}$alkyl.

In the definitions hereinabove and hereinafter the term halo defines fluoro, chloro, bromo and iodo; $C_{1-6}$alkyl is generic to straight and branch chained hydrocarbons having from 1 to 6 carbon atoms, such as, for example, methyl, ethyl, propyl, butyl, pentyl or hexyl and the possible branched isomers thereof; the term "$C_{1-6}$alkyl" in $C_{1-6}$alkyloxy, amino$C_{1-6}$alkyl, mono- and di($C_{1-6}$alkyl) amino$C_{1-6}$alkyl is as defined hereinabove.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The compounds of formula (I) containing acidic protons may also be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic saturated hydrocarbon radicals, in particular the substituents on the dioxolane or tetrahydrofuran ring, may have either the cis- or trans-configuration. Stereochemically isomeric forms of the compounds of formula (I) are obviously intended to be embraced within the scope of this invention.

Alk is appropriately methylene or ethanediyl;
$R^1$ is suitably fluoro, chloro or bromo, preferably fluoro;
$R^2$ is suitably hydrogen, fluoro, chloro or bromo, preferably fluoro;
$R^3$ is suitably hydrogen or phenyl, preferably hydrogen;
$R^4$ is suitably hydrogen or phenyl, preferably hydrogen;
$R^5$ is suitably hydrogen, methyl or ethyl;
$R^6$ is suitably hydrogen, methyl or ethyl; or
$R^5$ and $R^6$ are suitably taken together with the nitrogen atom to which they are attached to form a pyrrolidine ring or a substituted piperazine ring.

A and B taken together are suitably radicals of formula (a), (b) or (c).

Interesting compounds are those compounds of formula (I) wherein D is a radical of formula (D₁) or (D₂).

Particular compounds are those compounds of formula (I) wherein L is a radical formula (L₂) wherein $R^5$ and $R^6$ each independently are hydrogen or $C_{1-6}$alkyl; or when taken together with the nitrogen atom to which they are attached form a pyrrolidine, or a piperazine ring substituted with $C_{1-6}$alkyl or $C_{1-6}$alkyloxy on the 4-position of the piperazine ring.

More interesting compounds are those interesting compounds wherein L is a radical of formula (L₁).

Preferred compounds of formula (I) are those compounds of formula (I) wherein D is a radical of formula (D₁), wherein $R^1$ is chloro or fluoro and $R^2$ is hydrogen, chloro or fluoro; L is a radical of formula ($L_1$), wherein $R^3$ and $R^4$ each independently are phenyl or hydrogen.

The compounds of formula (I) wherein the substituents on the dioxolane or tetrahydrofuran have the cis-configuration, i.e. wherein the triazolmethylene substituent and the substituted phenyloxy methylene substituent are on the same side of the plane of the dioxolane or tetrahydrofuran ring, are preferred.

More preferred compounds are selected from:

(±)-ammonium cis-1-[[4-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-4,5-dihydro-5-oxo-1H-1,2,4-triazol-1-yl]methyl]-2,2-dimethylpropyl phosphate;

(±)-ammonium cis-1-[[4-[4-[4-[4-[[2-(2,4-dichlorophenyl)-2-(1H-1,2,4-triazol-1-yl-methyl)-1,3-dioxolan-4-yl]methoxy]phenyl]-1-piperazinyl]phenyl]-4,5-dihydro-5-oxo-1H-1,2,4-triazol-1-yl]methyl]-2,2-dimethylpropyl phosphate;

(±)-ammonium cis-1-[[4-[4-[4-[4-[[2-(4-chlorophenyl)-2-(1H-1,2,4-triazol-1-yl-methyl)-1,3-dioxolan-4-yl]methoxy]phenyl]-1-piperazinyl]phenyl]-4,5-dihydro-5-oxo-1H-1,2,4-triazol-1-yl]methyl]-2,2-dimethylpropyl phosphate(ester) monohydrate;

(±)-ammonium cis-1-[[4-[4-[4-[4-[[2-(4-fluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]methyl]-2,2-dimethylpropyl phosphate;

(±)-cis-1-[[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]methyl]-2,2-dimethylpropyl 4-methyl-1-piperazineacetate monohydrochloride; and (±)-cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2-[3,3-dimethyl-2-(phosphonooxy)butyl]-2,4-dihydro-3H-1,2,4-triazol-3-one hemihydrate.

Most preferred is (±)-cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2-[3,3-dimethyl-2-(phosphonooxy)butyl]-2,4-dihydro-3H-1,2,4-triazol-3-one, the stereochemically isomeric forms thereof and the base addition salts thereof.

The compounds of formula (I) may generally be prepared by O-acylation or O-phosphorylation of an intermediate alcohol of formula (II) with an acylating or phosphorylating reagent of formula (III), wherein $W^1$ is a reactive leaving group such as, hydroxy or halo. Said reaction may be performed following art-known acylation or phosphorylation procedures, for instance, by stirring the reactants in a reaction-inert solvent, optionally in admixture with a base to pick up the acid that is formed during the reaction.

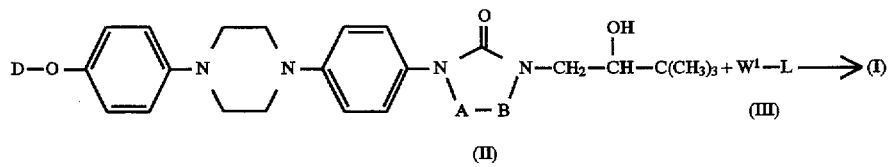

The compounds of formula (I) may also be prepared by O-alkylating a phenol of formula (IV) with an alkylating reagent of formula (V), wherein $W^2$ is a reactive leaving group such as halo, or a sulfonyloxy group. Said reaction may be performed by stirring the reactants in a reaction-inert solvent, optionally in admixture with a suitable base to pick up the acid that is formed during the reaction. In the compounds and intermediates mentioned hereinafter the substituents are as defined above, unless otherwise indicated.

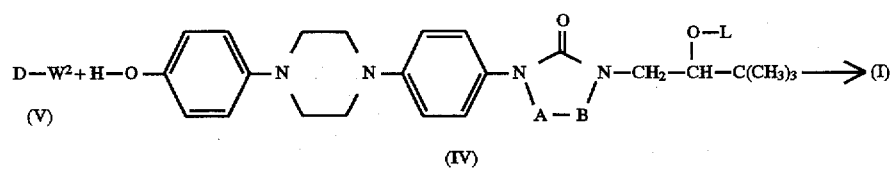

The preparation of intermediates of formula (V), wherein D is a radical of formula $D_1$, has been disclosed in U.S. Pat. No. 4,267,179. The preparation of intermediates of formula (V), wherein D is a radical of formula $D_3$, has been disclosed in EP-0,539,938.

The compounds of formula (I), wherein L is a radical of formula $L_2$, said compounds being represented by formula (I-b), may also be prepared by O-acylating an intermediate of formula (II) with a reagent of formula (VI) and subsequently reacting the thus obtained intermediate of formula (VII) with an amine of formula (VIII), thus yielding a compound of formula (I-b).

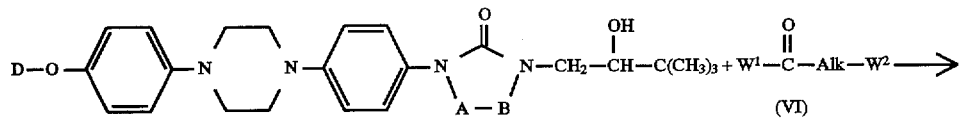

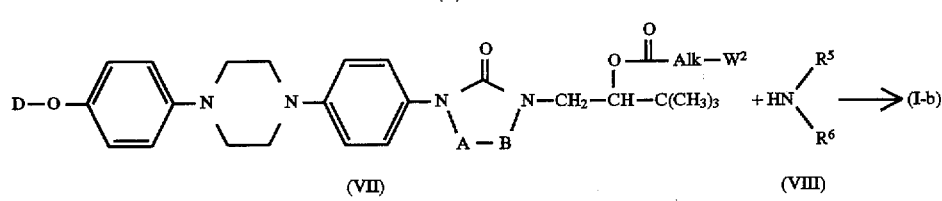

The compounds of formula (I) may also be converted into each other following art-known transformations. For instance, the compounds wherein L is a radical of formula $L_1$, said compounds being represented by formula (I-a), may be interconverted as follows. Compounds of formula (I-a) wherein $R^3$ and/or $R^4$ are $C_{1-6}$alkyl, phenyl or halophenyl may be transformed into compounds of formula (I-a), wherein $R^3$ and/or $R^4$ are hydrogen using art-known hydrolysis procedures, e.g. by reaction with sodium hydroxide in an appropriate solvent, e.g. water or 1,4-dioxane. The compounds of formula (I-b) may be interconverted into each other as follows.

Compounds of formula (I-b) wherein $R^5$ and/or $R^6$ are hydrogen may be transformed into compounds of formula (I-b), wherein $R^5$ and/or $R^6$ are $C_{1-6}$-alkyl, by art-known N-alkylation reactions. Compounds of formula (I-b), wherein $R^6$ is hydrogen may be converted into compounds of formula (I-b), wherein $R^6$ is $C_{1-6}$alkyloxycarbonyl by art-known N-acylation reactions. Conversely compounds of formula (I-b), wherein $R^6$ is $C_{1-6}$alkyloxycarbonyl may be converted into compounds of formula (I-b), wherein $R^6$ is hydrogen by art-known hydrolysis reactions.

The intermediates of formula (II) may be prepared by O-alkylating a reagent of formula (IX) with an alkylating reagent of formula (V) following O-alkylation procedures described hereinabove for the preparation of compounds of formula (I).

reagent of formula (V) following O-alkylation procedures described hereinabove for the preparation of compounds of formula (I), and subsequently reducing the thus formed intermediate of formula (XI). Said reduction may be performed by stirring the intermediate of formula (XI) with a reducing reagent, such as, for example, sodiumborohydride in a reaction-inert solvent, such as, for example, a halogenated hydrocarbon, e.g. dichloromethane, an alcohol, e.g. methanol and mixtures thereof.

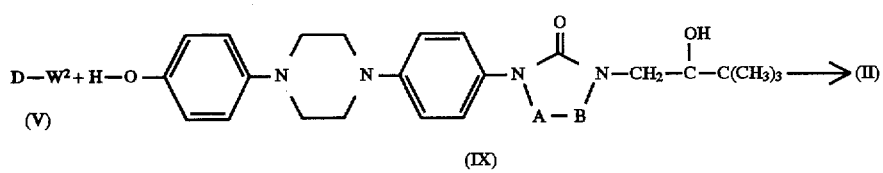

The intermediates of formula (II) may also be prepared by O-alkylating a reagent of formula (X) with an alkylating

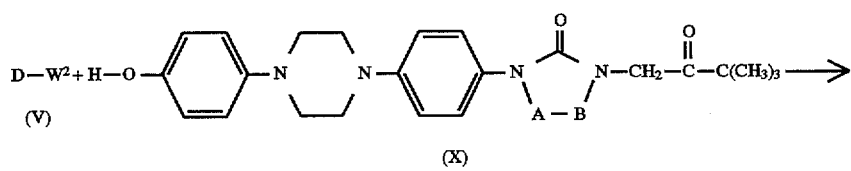

-continued

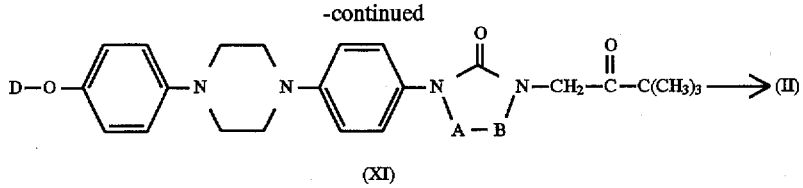

(XI)

The preparation of intermediates of formula (X) is disclosed in U.S. Pat. No. 4,931,444.

The intermediates of formula (XI) may also be prepared by N-alkylating an intermediate of formula (XII) following art-known N-alkylation procedures with an alkylating reagent of formula (XIII), wherein W³ is an appropriate leaving group, e.g. halo.

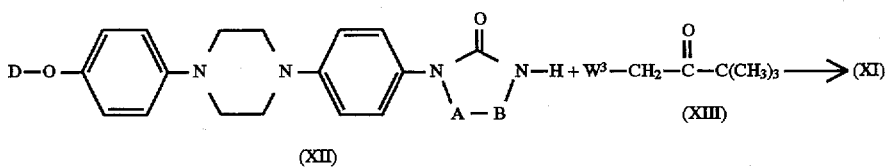

(XII)    (XIII)

Pure stereochemically isomeric forms of the compounds and the intermediates of this invention may be obtained by the application of art-known procedures. Diastereoisomers may be separated by physical separation methods such as selective crystallization and chromatographic techniques, e.g. liquid chromatography. Enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials. Stereochemically isomeric forms of the compounds of formula (I) are obviously intended to be included within the scope of the invention.

The compounds of formula (I), the pharmaceutically acceptable acid or base addition salts and the stereochemically isomeric forms thereof are useful agents for combating fungi and bacteria in vivo. Moreover the compounds of formula (I) are soluble in aqueous solutions, which makes then suitable for intravenous administration. Said compounds are found to be active against a wide variety of fungi, such as *Candida albicans, Aspergillus fumigatus, Cryptococcus neoformans, Coccidioides immitis, Histoplasma capsulatum, Blastomyces dermatitidis, Sporothrix schenkii, Fonsecaea sp., Microsporum canis, Paracoccidioides immitis, Trichophyton sp, Cladosporium carrionii,* and against bacteria such as, for example, *Erysipelotrix insidiosa,* Staphylococci such as *Staphylococcus haemolyticus* and Streptococci such as *Streptococcus pyogenes.*

The intermediates of formula (II), the pharmaceutically acceptable acid addition salts thereof and the stereochemically isomeric forms thereof are also useful in treating or preventing diseases associated with fungal infections and thus form a further aspect of the present invention. An interesting group of compounds of formula (II) are cis-4-[4-[4-[4-[[2-(2,4-difluorophenyl)-2-(1H-1,2,4-triazol-1-ylmethyl)-1,3-dioxolan-4-yl]-methoxy]-phenyl]-1-piperazinyl]phenyl]-2,4-dihydro-2-(2-hydroxy-3,3-dimethylbutyl)-3H-1,2,4-triazol-3-one, the pharmaceutically acceptable acid addition salts and the stereochemically isomeric forms thereof.

The present invention also provides compositions for treating or preventing fungal infections comprising an antifungally effective amount of a compound of formula (I) or an intermediate of formula (II) and a pharmaceutically acceptable carrier or diluent.

In view of their useful pharmacological properties, the subject compounds may be formulated into various pharmaceutical forms for administration purposes. To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carders such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, e.g. cyclodextrins, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Appropriate cyclodextrin derivatives are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl; hydroxy$C_{1-6}$alkyl, particularly hydroxyethyl, hydroxypropyl or hydroxy-butyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl or carboxy$C_{1-6}$alkyl-oxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD.

The term mixed ether denotes cyclodextrin derivatives wherein at least two cyclodextrin hydroxy groups are etherified with different groups such as, for example, hydroxypropyl and hydroxyethyl.

Those of skill in treating warm-blooded animals suffering from diseases caused by fungi and/or bacteria could easily determine the effective amount from the test results given herein. In general, it is contemplated that an effective amount would be from 0.01 mg/kg to 50 mg/kg body weight, and more preferably from 0.05 mg/kg to 20 mg/kg body weight.

EXPERIMENTAL PART

Of some compounds of formula (I), the absolute stereochemical configuration was not experimentally determined. In those cases the stereochemically isomeric form which was first isolated is designated as "A" and the second as "B".

A. Preparation of the Intermediates

Example 1

To a stirred and cooled (ice-bath) mixture of 2-(2,4-difluorophenyl)-3-(1H-1,2,4-triazol-1-yl)-1,2-propanediol (30 g), methanesulfonic acid (50 ml) and dichloromethane (500 ml) was added dropwise 1-bromo-2,2-diethoxyethane (17 ml). After stirring for 3 hours at 0° C., the reaction mixture was poured into sodium hydrogen carbonate (aq.). The product was extracted with dichloromethane and the extract was dried, filtered and evaporated. The residue was purified twice by column chromatography (silica gel; $CHCl_3/CH_3OH$ 99:1; $CHCl_3/CH_3OH$/hexane/ $CH_3COOC_2H_5$ 49:1:20:30). The eluent of the desired fraction was evaporated, yielding 8 g (19.0%) of cis-1-[[2-(bromomethyl)-4-(2,4-difluorophenyl)-1,3-dioxolan-4-yl]methyl]-1H-1,2,4-triazole; mp. 76.3° C. (interm. 1).

Example 2

A mixture of 2-(3,3-dimethyl-2-oxobutyl)-2,4-dihydro-4-[4-[4-(4-hydroxyphenyl)-1-piperazinyl]phenyl]-3H-1,2,4-triazol-3-one (0.01 mol) and sodium hydride (0.012 mol) in N,N-dimethylformamide (100 ml) was stirred under nitrogen at 70° C. Intermediate (1) (0.012 mol) was added and the mixture was stirred further overnight. Intermediate (1) (2 g) was added again and the mixture was stirred at 70° C. for 6 hours and then at room temperature overnight. The mixture was evaporated, the residue was taken up in dichloromethane and washed. The organic layer was dried, filtered off and evaporated. The residue was purified by column chromatography over silica gel (eluent: $CH_2Cl_2$/hexane/ ethyl acetate 50/20/30). The pure fractions were collected and evaporated. The residue was purified further on a glass filter over silica gel/NH₂ (eluent: $CH_2Cl_2$). The pure fractions were collected and evaporated. The residue was crystallized from ethyl acetate, yielding 2.2 g (31%) of (±)-cis-4-[4-[4-[4-[[4-(2,4-difluorophenyl)-4-(1H-1,2,4-triazol-1-ylmethyl)-1,3-dioxolan-2-yl]methoxy]phenyl]-1-piperazinyl]phenyl]-2-(3,3-dimethyl-2-oxobutyl)-2,4-dihydro-3H-1,2,4-triazol-3-one; 197.1° C. (interm. 2).

Example 3 a) A mixture of cis-2-(2,4-difluorophenyl)-2-(1H-1,2,4-triazol-1-ylmethyl)-1,3-dioxolane-4-methanol (0.2 mol) in pyridine (400 ml) and dichloromethane (250 ml) was stirred at room temperature. A solution of 4-cyanobenzoyl chloride (0.22 mol) in dichloromethane (150 ml) was added dropwise. The reaction mixture was stirred for 24 hours at room temperature. The reaction mixture was diluted with water. The organic layer was separated, dried (MgSO₄), filtered and the solvent was evaporated. The residue was crystallized from methylbenzene. The crystals were filtered off and dried. This fraction was purified by column chromatography over a Chiracell OD column (eluent: $C_2H_5OH$). The first peak fractions were combined and the solvent was evaporated. The residue was crystallized from 4-methyl-2-pentanone. The crystals were filtered off and dried, yielding 21.2 g (24.9%) of (+)-cis-[2-(2,4-difluorophenyl)-2-(1H-1,2,4-triazol-1-ylmethyl)-1,3-dioxolan-4-yl]methyl 4-cyanobenzoate; mp. 146.3° C.; $[\alpha]_D^{20}=+22.71°$ (c=0.5% in methanol) (interm. 3). The second peak fractions were combined and the solvent was evaporated. The residue was crystallized from 4-methyl-2-pentanone. The crystals were filtered off and dried, yielding 21.4 g (25.1%) (−)-cis-[2-(2,4-difluorophenyl)-2-(1H-1,2,4-triazol-1-ylmethyl)-1,3-dioxolan-4-yl]-methyl 4-cyanobenzoate; mp. 144.0° C.; $[\alpha]_D^{20}=-22.64°$ (c=0.5% in methanol) (interm. 4).

b) A mixture of intermediate (3) (0.049 mol) and sodium hydroxide 50% (0.059 mol) in water (300 ml) and 1,4-dioxane (300 ml) was stirred for 24 hours at room temperature. The solvent was evaporated. The residue was partitioned between water and dichloromethane. The organic layer was separated, dried (MgSO₄), filtered and the solvent was evaporated. The residue was crystallized from 4-methyl-2-pentanone. The crystals were filtered off and dried, yielding 10.1 g (70%) of (+)-cis-2-(2,4-difluorophenyl)-2-(1H-1,2,4-triazol-1-ylmethyl)-1,3-dioxolane-4-methanol; mp. 123.0° C.; $[\alpha]_D^{20}=+16.58°$ (c=0.5% in methanol) (interm. 5)

In a similar manner was also prepared: (−)-cis-2-(2,4-difluorophenyl)-2-(1H-1,2,4-triazol-1-ylmethyl)-1,3- dioxolane-4-methanol; mp. 123.2° C.; [α]$_D^{20}$=−15.97° (c=0.5% in methanol) (interm. 6).

c) A mixture of intermediate (5) (0.02 mol) and N,N-diethylethanamine (0.03 mol) in dichloromethane (50 ml) was stirred at room temperature. Methanesulfonyl chloride (0.03 mol) was added dropwise and the reaction mixture was stirred overnight at room temperature. The solvent was evaporated. The residue was partitioned between methylbenzene and water. A precipitate was formed, which was filtered off, dried and recrystallized from 2,2'-oxybispropane/4-methyl-2-pentanone. The precipitate was filtered off and dried (vacuum; 40° C.), yielding two fractions. Those fractions were combined and recrystallized from 2,2'-oxybispropane/4-methyl-2-pentanone. The precipitate was filtered off and dried (vacuum; 40° C.), yielding 5.88 g (78.3%) of (+)-cis-2-(2,4-difluorophenyl)-2-(1H-1,2,4-triazol-1-ylmethyl)-1,3-dioxolane-4-methanol methanesulfonate(ester); [α]$_D^{20}$=+15.50° (c=0.2% in methanol) (interm. 7).

In a similar manner was also prepared: (−)-cis-2-(2,4-difluorophenyl)-2-(1H-1,2,4-triazol-1-ylmethyl)-1,3-dioxolane-4-methanol methanesulfonate (ester); [α]$_D^{20}$=−14.50° (c=0.2% in methanol) (interm. 8).

Example 4 a) A mixture of 2,4-dihydro-2-(2-hydroxy-3,3-dimethylbutyl)-4-[4-[4-(4-hydroxyphenyl)-1-piperazinyl]phenyl]-3H-1,2,4-triazol-3-one (0.046 mol), 2-(chlorodimethylsilyl)-2-methylpropane (0.063 mol) and 1H-imidazole (0.19 mol) in N,N-dimethylformamide (300 ml) was stirred for 4 hours at 50° C. The reaction mixture was poured out into water. The resulting precipitate was filtered off and dried, yielding 21 g (83%) of product. A sample (1 g) was triturated in 2,2'-oxybispropane, filtered off and dried, yielding 0.7 g of (±)-4-[4-[4-[4-[[(1,1-dimethylethyl)dimethylsilyl]oxy]phenyl]-1-piperazinyl]phenyl]-2-(2-hydroxy-3,3-dimethylbutyl)-2,4-dihydro-3H-1,2,4-triazol-3-one; mp. 196.1° C. (interm. 9).

b) Intermediate (9) (0.036 mol, mixture of enantiomers) was separated in it's enantiomers by column chromatography over a Chiracell® OD column (eluent: n-hexanes/2-propanol 65/35). The fraction, corresponding to a first chromatographic peak, was collected and the solvent was evaporated. The residue was crystallized from acetonitrile. The precipitate was filtered off and dried (vacuum; 50° C.); yielding 1.56 g (7.8%) of (−)-4-[4-[4-[4-[[(1,1-dimethylethyl)dimethylsilyl]oxy]phenyl]-1-piperazinyl]phenyl]-2-(2-hydroxy-3,3-dimethylbutyl)-2,4-dihydro-3H-1,2,4-triazol-3-one (interm. 10). The fraction, corresponding to a second chromatographic peak, was collected and the solvent was evaporated. The residue was crystallized from acetonitrile. The precipitate was filtered off and dried (vacuum; 50° C.); yielding 2.28 g (11.4%) of (+)-4-[4-[4-[4-[[(1,1-dimethylethyl)dimethylsilyl]oxy]phenyl]-1-piperazinyl]phenyl]-2-(2-hydroxy-3,3-dimethylbutyl)-2,4-dihydro-3H-1,2,4-triazol-3-one (interm. 11).

c) A mixture of intermediate (10) (0.0135 mol) in dichloromethane (150 ml) was stirred until complete dissolution. A solution of tetrabutylammonium fluoride in tetrahydrofuran (0.015 mol) was added in one portion and the reaction mixture was stirred for 1 hour at room temperature. The mixture was diluted with water (150 ml) and stirred for 1 hour. The precipitate was filtered off and recrystallized from 2-methoxyethanol. The product was filtered off and dried (vacuum; 60° C.), yielding 4.7 g (79.6%) of (−)-2,4-dihydro-2-(2-hydroxy-3,3-dimethylbutyl)-4-[4-[4-(4-hydroxyphenyl)-1-piperazinyl]phenyl]-3H-1,2,4-triazol-3-one; [α]$_D^{20}$=−3.14° (c=0.1% in N,N-dimethylformamide) (interm. 12).

In a similar manner was also prepared: (+)-2,4-dihydro-2-(2-hydroxy-3,3-dimethylbutyl)-4-[4-[4-(4-hydroxyphenyl)-1-piperazinyl]phenyl]-3H-1,2,4-triazol-3-one; [α]$_D^{20}$=+6.22° (c=0.1% in N,N-dimethylformamide) (interm. 13).

Example 5

A mixture of cis-4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-3H-1,2,4-triazol-3-one (9.3 g), 1-bromo-3,3-dimethyl-2-butanone (2.8 g), sodium carbonate (6.4 g) and 1,3-dimethyl-2-imidazolidinone (52.2 g) was stirred for 5 hours at 100° C. After cooling, the reaction mixture was poured into water. The formed precipitation was filtered off and dissolved in dichloromethane. This solution was dried, filtered and evaporated. The residue was purified by column chromatography (silica gel; CH$_2$Cl$_2$/CH$_3$OH 98:2). The eluent of the desired fraction was evaporated and the residue was crystallized from 4-methyl-2-pentanone. The product was filtered off and dried, yielding 5.5 g (51.3%) of cis-4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2-(3,3-dimethyl-2-oxobutyl)-2,4-dihydro-3H-1,2,4-triazol-3-one; mp. 176.2° C. (interm. 14).

Example 6

To a mixture of intermediate (14) (4.5 g), 1,4-dioxane (40 ml) and methanol (3 ml) was added dropwise a solution of sodium tetrahydroborate (0.3 g) in some water. After stirring overnight, the reaction mixture was poured into water and acidified with acetic acid to ±pH 5. The precipitate was filtered off, washed with water, dried and purified by column chromatography (silica gel; CH$_2$Cl$_2$/CH$_3$OH 98:2). The eluent of the desired fraction was evaporated and the residue was crystallized from 2-propanol, yielding 2.2 g (48.7%) of cis-4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-2-(2-hydroxy-3,3-dimethylbutyl)-3H-1,2,4-triazol-3-one; mp. 196.4° C. (interm. 15).

Example 7

Sodium hydride (0.00675 mol) was added portionwise to a mixture of intermediate (12) (0.00595 mol) in N,N-dimethylformamide (50 ml), stirred at room temperature. The mixture was stirred for 90 minutes at room temperature. Intermediate (7) (0.0054 mol) was added and the reaction mixture was stirred for 4 hours at 60° C. The mixture was cooled and the solvent was evaporated. The residue was partitioned between dichloromethane and water. The organic layer was separated, dried, filtered and the solvent was evaporated. The residue was purified by column chromatography over an aminopropyl column (eluent: CH$_2$Cl$_2$/CH$_3$OH 96/4). The pure fractions were collected and the solvent was evaporated. The residue was crystallized from 4-methyl-2-pentanone. The precipitate was filtered off and dried (vacuum; 50° C.), yielding 1.67 g (43.1%) of (+)-[cis (+)(B)]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(2-hydroxy-3,3-dimethylbutyl)-3H-1,2,4-triazol-3-one; mp. 191.9° C.; [α]$_D^{20}$=+12.03° (c=0.5% in dichloromethane) (interm.20).

TABLE 1

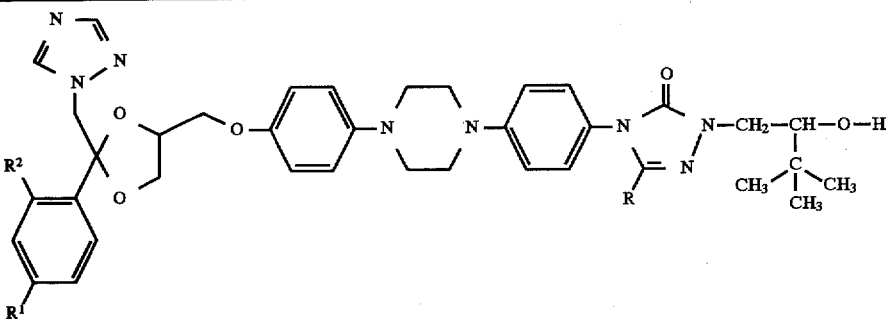

| Int. No. | Ex. No. | R | R¹ | R² | Physical data |
|---|---|---|---|---|---|
| 15 | 6 | H | F | F | mp. 196.4° C./cis |
| 16 | 6 | H | Cl | Cl | mp. 187.1° C./cis |
| 17 | 6 | H | Cl | H | mp. 201.5° C./cis |
| 18 | 6 | H | F | H | mp. 213.2° C./cis |
| 19 | 6 | H | F | H | mp. 211.1° C./trans |
| 20 | 7 | H | F | F | mp. 191.9° C./$[\alpha]_D^{20}$ = +12.03° (c = 0.5% in dichloromethane)/ (+)-[cis(+)(B)] |
| 21 | 7 | H | F | F | mp. 213.2° C./$[\alpha]_D^{20}$ = −7.89° (c = 0.5% in dichloromethane) (−)-[cis(−)(B)] |
| 22 | 7 | H | F | F | mp. 212.5° C./$[\alpha]_D^{20}$ = +8.38° (c = 0.5% in dichloromethane) (+)-[cis(+)(A)] |
| 23 | 7 | H | F | F | mp. 185.6° C./$[\alpha]_D^{20}$ = −5.08° (c = 0.5% in N,N-dimethylformamide) (−)-[cis(−)(A)] |

Example 8

A mixture of intermediate (2) (0.0025 mol) in dichloromethane (100 ml) and methanol (100 ml) was stirred at room temperature. Sodium borohydride (0.005 mol) was added and the mixture was stirred for 4 hours. Water (100 ml) was added, the mixture was stirred overnight and separated. The organic layer was washed, dried, filtered off and evaporated. The residue was crystallized from ethyl acetate, yielding 1.6 g (89.3%) of (±)-cis-4-[4-[4-[4-[[4-(2,4-difluorophenyl)-4-(1H-1,2,4-triazol-1-ylmethyl)-1,3-dioxolan-2-yl]methoxy]phenyl]-1-piperazinyl]phenyl]-2,4-dihydro-2-(2-hydroxy-3,3-dimethylbutyl)-3H-1,2,4-triazol-3-one; mp. 184.1° C. (interm. 24).

Example 9

A mixture of 2,4-dihydro-2-(2-hydroxy-3,3-dimethylbutyl)-4-[4-[4-(4-hydroxyphenyl)-1-piperazinyl]phenyl]-3H-1,2,4-triazol-3-one (0.0035 mol), cis-[5-(2,4-difluorophenyl)tetrahydro-5-(1H-1,2,4-triazol-1-ylmethyl)-3-furanmethanol 4-methylbenzenesulfonate (the preparation of which is described in European Patent Application 0,539, 938) (0.0033 mol) and sodium hydroxide (0.01 mol) in N,N-dimethylformamide (50 ml) was stirred under nitrogen at 50° C. for 4 hours and the mixture was stirred further under nitrogen at 60° C. for 2 hours. The mixture was cooled and water was added. The product was crystallized out, filtered off and dried. The residue was purified on a glass filter over silica gel (eluent: CH₂Cl₂/CH₃OH 99/1). The pure fractions were collected and evaporated. The residue was recrystallized from dioxane/2,2'-oxybispropane, yielding 1.7 g (72%) of (±)-cis-4-[4-[4-[4-[[5-(2,4-difluorophenyl) tetrahydro-5-(1H-1,2,4-triazol-1-ylmethyl)-3-furanyl] methoxy]phenyl]-1-piperazinyl]phenyl]-2,4-dihydro-2-(2-hydroxy-3,3-dimethylbutyl)-3H-1,2,4-triazol-3-one; mp. 210.8° C. (interm. 25).

Example 10

Chloroacetyl chloride (0.02 mol) was added to a stirring mixture of intermediate (15) (0.0082 mol) in dichloromethane (100 ml). Pyridine (0.037 mol) was added dropwise and the mixture was stirred for 2 hours. Hydrochloric acid 1N (50 ml) was added, the mixture was stirred for 2 hours. The organic layer was washed with a sodium hydrogen carbonate-solution, dried, filtered off and evaporated. The residue was crystallized and triturated in 4-methyl-2-pentanone/2,2'-oxybispropane, yielding 6.3 g (96.8%) of product. A sample (1 g) was recrystallized from 4-methyl-2-pentanone, yielding 0.6 g of (±)-cis-1-[[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]methyl]-2,2-dimethylpropyl chloroacetate (interm. 26).

Example 11

A mixture of (±)-2,4-dihydro-4-(2-hydroxy-3,3-dimethylbutyl)-2-[4-[4-(4-hydroxyphenyl)-1-piperazinyl] phenyl]-3H-1,2,4-triazol-3-one (0.0068 mol), (±)-cis-2-(2,4-difluorophenyl)-2-(1H-1,2,4-triazol-1-ylmethyl)-1,3-dioxolane-4-methanol methanesulfonate (ester) (0.0082 mol) and sodium hydroxide (0.025 mol) in N,N-dimethylformamide (100 ml) was stirred under nitrogen at 60° C. for 4 hours. The mixture was cooled, water was added and the mixture was stirred. The precipitate was filtered off and dried. The residue was purified on a glass filter over silica gel (eluent: CH₂Cl₂/CH₃OH/ethyl acetate/n-hexane 48/2/30/20). The pure fractions were collected and evaporated. The residue was recrystallized from 4-methyl-2- pentanone, yielding 1.1 g (22%) of (±)-cis-2-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-4-(2-hydroxy-3,3-dimethyl-butyl)-3H-1,2,4-triazol-3-one; mp. 201.2° C. (interm. 27).

Example 12

A mixture of (±)-cis-1-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-3-(3,3-dimethyl-2-oxobutyl)-1,3-dihydro-2H-imidazol-2-one (0.0036 mol) in methanol (50 ml) and dichloromethane (50 ml) was stirred. Sodium borohydride (0.01 mol) was added and the mixture was stirred at room temperature for 1 hour. Water (100 ml) was added and the mixture was stirred for 1 hour. The mixture was separated and the aqueous layer was extracted with dichloromethane. The organic layer was dried, filtered off and evaporated. The residue was purified on a glass filter over silica gel (eluent: CH$_2$Cl$_2$/CH$_3$OH 99/1). The pure fractions were collected and evaporated. The residue was recrystallized from 4-methyl-2-pentanone, yielding 1.9 g (73%) of (±)-cis-1-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-3-(2-hydroxy-3,3-dimethylbutyl)-2-imidazolidinone; mp. 196.8° C. (interm. 29).

ml) was stirred at room temperature for 6 hours. Water (200 ml) was added, the mixture was filtered over dicalite and the filtrate was acidified with hydrochloric acid till pH=2–3. The mixture was extracted three times with dichloromethane. The combined organic layers were dried, filtered off and evaporated. The residue was dissolved in a saturated sodium hydrogen carbonate solution (100 ml), washed with 2,2'-oxybispropane and extracted twice with dichloromethane (500 ml) and methanol (100 ml). The combined organic layers were dried, filtered off and evaporated. The residue was crystallized from 2-propanol and a little water, yielding 1.2 g (46%) of (±)-cis-1-[[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]methyl]-2,2-dimethylpropyl phenyl sodium phosphate; mp. 167.0° C. (comp. 2).

Example 15

A mixture of compound (1) (0.0038 mol) and sodium hydroxide 50% solution (5 g) in 1,4-dioxane (100 ml) was stirred at room temperature overnight. Water (600 ml) was added, the mixture was filtered over dicalite and the filtrate was acidified with hydrochloric acid. The precipitate was filtered off (*) and the filtrate was extracted with dichloromethane. The mixture was evaporated. The residue, the

TABLE 2

| Interm. No. | Ex. No. | A—B | Physical data |
| --- | --- | --- | --- |
| 27 | 11 | —N=CH— | mp. 201.2° C. |
| 28 | 11 | —(C=O)—C(CH$_3$)$_2$— | mp. 141.8° C. |
| 29 | 12 | —CH$_2$—CH$_2$— | mp. 196.8° C. |
| 30 | 11 | —CH=N | mp. 147.6° C./(+)-[(B-cis),B]/[α]$_D^{20}$ = +1.20° (c = 0.5% in methanol) |

B. Preparation of the Final Compounds

Example 13

A mixture of intermediate (15) (0.0014 mol), diphenyl chlorophosphate (0.003 mol) and N,N-dimethyl-4-pyridinamine (1 g) in dichloromethane (30 ml) was stirred at room temperature for 2 hours. The mixture was purified on a glass filter over silica gel (eluent: CH$_2$Cl$_2$/CH$_3$OH 98/2). The pure fractions were collected and evaporated. The residue was recrystallized from 4-methyl-2-pentanone/2,2'-oxybispropane, yielding 1.1 g (83%) of (±)-cis-1-[[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]methyl]-2,2-dimethylpropyl diphenyl phosphate; mp. 170.8° C. (comp. 1).

Example 14

A mixture of compound (1) (0.0029 mol) and a dispersion of sodium hydroxide 50% solution (5 g) in 1,4-dioxane (50 precipitate (*) and sodium hydroxide 50% (5 g) were stirred at 60° C. for 24 hours. Sodium hydroxide 50% (3 g) was added again and the mixture was stirred at 60° C. for 48 hours. The mixture was cooled, acidified with hydrochloric acid 1N till pH=4 and extracted with dichloromethane. The combined organic layers were dried, filtered off and evaporated. The residue was boiled up in methanol (70 ml), filtered off and methanol/ammonia (20 ml) was added to the filtrate. The mixture was boiled up in 2-propanol (20 ml) and cooled. The mixture was filtered off, the precipitate was dissolved in water (200 ml) and washed twice with ethyl acetate. The aqueous layer was acidified with hydrochloric acid 1N and extracted three times with dichloromethane. The combined organic layers were dried, filtered off and evaporated. The residue was dissolved in methanol (70 ml) and methanol/ammonia (10 ml) was added. The precipitate was filtered off and dried, yielding 1.6 g (51%) of (±)-ammonium cis-1-[[4-[4-[4-[4-[[2-(2,4-difluorophenyl)-2-(1H-1,2,4-triazol-1-ylmethyl)-1,3-dioxolan-4-yl]methoxy]

phenyl]-1-piperazinyl]phenyl]-4,5-dihydro-5-oxo-1H-1,2, 4-triazol-1-yl]methyl]-2,2-dimethylpropyl phosphate; mp. 189.6° C. (comp. 3).

Example 16

Sodium hydroxide 50% (1.4 mol) was added to a suspension of (±)-cis-1-[[4-[4-[4-[4-[[2-(2,4-difluorophenyl)-2-(1H-1,2,4-triazol-1-ylmethyl)-1,3-dioxolan-4-yl]methoxy] phenyl]-1-piperazinyl]phenyl]-4,5-dihydro-5-oxo-1H-1,2, 4-triazol-1-yl]methyl]-2,2-dimethylpropyl diphenyl phosphate (0.07 mol) in 1,4-dioxane (1400 ml) under N₂ flow. . The resulting suspension was heated to 60° C. The reaction solution was stirred for 92 hours at 60° C. The mixture was allowed to cool to 25° C. The mixture was poured out into distilled water (5.25 liter) and this mixture was stirred vigorously for 1 hour. The mixture was filtered. The filtrate was acidified (pH=2.7) with hydrochloric acid and recipitation resulted. The aqueous layer was extracted with CH₂Cl₂ (1×2 liter; 1×1.5 liter). The combined extracts were dried (Na₂SO₄), filtered and the solvent was evaporated. The residue (71.02 g; 124.7% yield) was stirred in 2-propanol (1050 ml), heated to reflux temperature, stirred and refluxed for 5 min, cooled on an ice bath while stirring vigorously, cooled to 20° C. and stirring was continued overnight. The precipitate was filtered off, washed with 2-propanol (1×35 ml), diisopropylether (2×35 ml) and dried (vacuum; 50° C.), yielding 48.10 g of (±)-cis-4-[4-[4-[4-[[2-(2,4-difluorophenyl)-2-(1H-1,2,4-triazol-1-ylmethyl)-1, 3-dioxolan-4-yl]methoxy]phenyl]-1-piperazinyl]phenyl]-2-[3,3-dimethyl-2-(phosphonooxy)butyl]-2,4-dihydro-3H-1,2, 4-triazol-3-one hemihydrate; mp. 156.2° C. (comp. 17).

Example 17

1-Deoxy-1-(methylamino)-D-glucitol (0.02 mol) was added to a mixture of compound (17) (0.005 mol) in water (70 ml) and the mixture was stirred until complete dissolution (30 min). The solvent was evaporated. Toluene was added and azeotroped on the rotary evaporator. Ethanol (250 ml) was added and the mixture was stirred vigorously. The mixture was cooled on an ice bath and stirred for 1 hour and precipitation resulted. The mixture was allowed to warm to room temperature (20° C.). The mixture was stirred for 18 hours at room temperature and the resulting precipitate was filtered off, washed with ethanol, with diisopropylether (2×10 ml) and dried (vacuum; 50° C.), yielding: 6.14 g (1). The filtrate was evaporated. The residue was dried (vacuum; 50° C.), yielding: 1.98 g (2). Fraction (1) was ground, stirred vigorously for 5 hours in ethanol (200 ml) and the resulting precipitate was filtered off, washed with ethanol (4×5 ml) and dried (vacuum; 45°–50° C.; 64 hours), yielding: 4.98 g (±)-cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2-[3,3-dimethyl-2-(phosphonooxy) butyl]-2,4-dihydro-3H-1,2,4-triazol-3-one 1-deoxy-1-(methylamine)-D-glucitol (1:2).monohydrate (comp. 18)

Example 18

A mixture of intermediate (26) (0.0025 mol) and pyrrolidine (0.014 mol) in N,N-dimethylformamide (50 ml) was stirred at room temperature for 4 hours. Water was added and the mixture was stirred. The precipitate was filtered off, washed with water and purified on a glass filter over silica gel (eluent 1: CH₂Cl₂/CH₃OH 98/2 and eluent 2: CH₂Cl₂/ CH₃OH 95/5). The suitable fractions were collected and evaporated. The residue was dissolved in dichloromethane (100 ml) and stirred with hydrochloric acid 0.4N (50 ml). The mixture was separated and the aqueous layer was extracted four times with dichloromethane. The combined organic layers were dried, filtered off and evaporated. The oily residue was dissolved in dichloromethane, washed with a sodium hydrogen carbonate solution, dried, filtered off and evaporated. The residue was crystallized from 4-methyl-2-pentanone, yielding 1.1 g (53% ) of (±)-cis-1-[[4-[4-[4-[4-[[2-(2,4-difluorophenyl)-2-(1H-1,2,4-triazol-1-ylmethyl)-1, 3-dioxolan-4-yl]methoxy]phenyl]-1-piperazinyl]phenyl]-4, 5-dihydro-5-oxo-1H-1,2,4-triazol-1-yl]methyl]-2,2-dimethylpropyl 1-pyrrolidineacetate; mp. 156.7° C. (comp. 28).

Example 19

A mixture of intermediate (16) (0.0066 mol), 4-methyl-1-piperazineacetic acid dihydrochloride (0.013 mol), 1,3-dicyclohexylcarbodiimide (0.026 mol) and N,N-dimethyl-4-pyridinamine 0.026 mol) in dichloromethane (100 ml) was stirred at room temperature for 4 hours. Hydrochloric acid 1N (200 ml) was added and the mixture was stirred for 1 hour. The precipitate was filtered off, water (600 ml) was added and the mixture was separated (*). The aqueous layer was washed with dichloromethane (100 ml) and separated. The aqueous layer was neutralized with pyridine and extracted five times with dichloromethane. The combined organic layers were dried, filtered off and evaporated, yielding 4.5 g of fraction 1. (*) The organic layer was washed with hydrochloric acid 1N (100 ml) and separated. The aqueous layer was neutralized with pyridine and extracted twice with dichloromethane. The combined organic layers were dried, filtered off and evaporated, yielding 2 g of fraction 2. Fractions 1 and 2 were put together and recrystallized from (acetonitrile 2% water)/2,2'oxybispropane, yielding 3.8 g (61%) of (±)-cis-1-[[4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]methyl]-2,2-dimethylpropyl 4-methyl-1-piperazineacetate . monohydrochloride . hemihydrate; mp. 156.0° C. (comp. 32).

Example 20

A mixture of compound (17) (0.0034 mol) in a solution of hydrochloric acid in 2-propanol (10 ml) and dichloromethane (60 ml) was stirred and refluxed for 30 minutes. The mixture was evaporated. The residue was dissolved in water and filtered off. The filtrate was neutralized with a sodium hydrogen carbonate solution and extracted with dichloromethane. The organic layer was dried, filtered off and evaporated. The residue was dissolved in hydrochloric acid 0.5N (50 ml) and washed three times with ethyl acetate (100 ml). The aqueous layer was neutralized with pyridine and extracted three times with dichloromethane. The combined organic layers were dried, filtered off and evaporated. The residue was crystallized from acetonitrile and a little N,N-dimethylformamide, yielding 1.3 g (46%) of (±)-cis-1-[[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]methyl]-2,2-dimethylpropyl β-alanine monohydrochloride; mp. 217.9° C. (comp. 36).

Example 21

A mixture of (±)-cis-N-[1-[3-[1-[[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5- dihydro-5-oxo-1H-1,2,4-triazol-1-yl]methyl]-2,2-dimethylpropoxy]-3-oxopropyl]-1,4-dihydro-4-pyridinylidene]-N-methylmethanaminium chloride monohydrate (0.0024 mol) and pyrrolidine (0.01 mol) in N,N-dimethylformamide (50 ml) was stirred at room temperature for 1 hour. The mixture was poured into water and extracted three times with dichloromethane. The combined organic layers were washed with water, dried, filtered off and evaporated. The residue was dissolved in hydrochloric acid 0.5N (500 ml) and washed three times with ethyl acetate (100 ml). The aqueous layer was neutralized with pyridine and extracted three times with dichloromethane. The combined organic layers were dried, filtered off and evaporated. The residue was crystallized from 4-methyl-2-pentanone and water (0.5 ml). The residue was purified on a glass filter over silica gel (eluent: $CH_2Cl_2/CH_3OH$ 96/4). The suitable fractions were collected and evaporated. The residue was dissolved in hydrochloric acid 1N (50 ml), neutralized with pyridine and extracted five times with dichloromethane. The combined organic layers were dried, filtered off and evaporated. The residue was crystallized from 4-methyl-2-pentanone and water (5 drops), yielding 1.1 g (51%) of (±)-cis-1-[[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]methyl]-2,2-dimethylpropyl 1-pyrrolidinepropanoate . monohydrochloride . monohydrate; mp. 154.4° C. (comp. 37)

TABLE 3

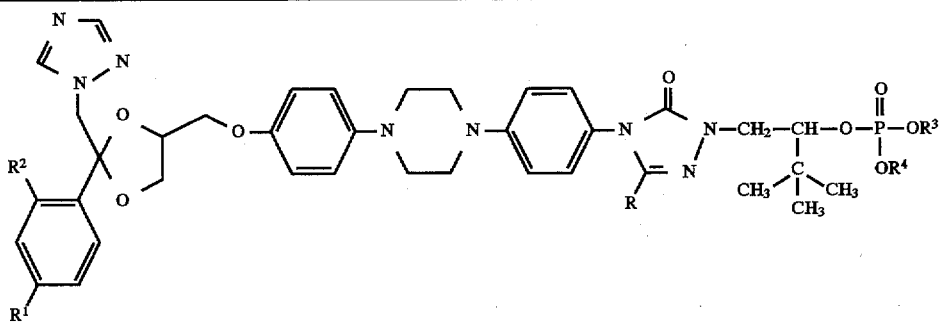

| Co. No. | Ex. No. | R | R¹ | R² | R³ | R⁴ | Physical data |
|---|---|---|---|---|---|---|---|
| 1 | 13 | H | F | F | $C_6H_5$ | $C_6H_5$ | mp. 170.8° C. |
| 2 | 14 | H | F | F | H | $C_6H_5$ | mp. 167.0° C./Na⁺ |
| 3 | 15 | H | F | F | H | H | mp. 189.6° C./NH₄⁺ |
| 4 | 13 | H | Cl | Cl | $C_6H_5$ | $C_6H_5$ | mp. 167.1° C. |
| 5 | 15 | H | Cl | Cl | H | H | mp. 188.2° C./NH₄⁺ |
| 6 | 13 | H | Cl | H | $C_6H_5$ | $C_6H_5$ | mp. 174.2° C. |
| 7 | 15 | H | Cl | H | H | H | mp. 195.5° C./NH₄⁺ |
| 8 | 13 | H | F | H | $C_6H_5$ | $C_6H_5$ | mp. 184.6° C. |
| 9 | 15 | H | F | H | H | H | mp. 159.8° C./NH₄⁺ |
| 10 | 13 | H | F | F | $C_6H_5$ | $C_6H_5$ | mp. 147.6° C. $[\alpha]_D^{20} = +1.20°$ (c = 0.5% in methanol) (+)-[(B-cis),B] |
| 11 | 15 | H | F | F | H | H | mp. 200.7° C./NH₄⁺ $[\alpha]_D^{20} = -15.8°$ (c = 0.1% in DMF) (+)-[(B-cis),B] |
| 12 | 13 | H | F | F | $C_6H_5$ | $C_6H_5$ | mp. 76.6° C. $[\alpha]_D^{20} = -15.89°$ (c = 0.1% in methanol) (−)-[(A-cis),B] |
| 13 | 13 | H | F | F | $C_6H_5$ | $C_6H_5$ | mp. 76.7° C. $[\alpha]_D^{20} = 13.62°$ (c = 0.1% in methanol) (−)-[(B-cis),A] |
| 14 | 13 | H | F | F | $C_6H_5$ | $C_6H_5$ | mp. 145.7° C. $[\alpha]_D^{20} = -3.52°$ (c = 0.1% in methanol) (−)-[(A-cis),A] |
| 15 | 13 | H | F | F | $C_6H_5$ | $C_6H_5$ | cis |
| 16 | 15 | H | F | F | H | H | mp. 201.3° C./NH₄⁺ cis |
| 17 | 16 | H | F | F | H | H | mp. 156.2° C. cis 1/2H₂O |
| 18 | 17 | H | F | F | H | H | mp. 117.6° C. cis .2CH₃—NH—CH₂—(C—OH)₄—CH₂—OH |
| 19 | 17 | H | F | F | H | H | mp. 184.7° C./cis C(CH₂—OH)₃NH₂ |
| 20 | 17 | H | F | F | H | H | mp. 251.7° C./.2Na⁺ cis. 7/2H₂O |
| 21 | 15 | H | F | F | H | H | mp. 202.7° C./NH₄⁺/ $[\alpha]_D^{20} = 51.72°$ |

TABLE 3-continued

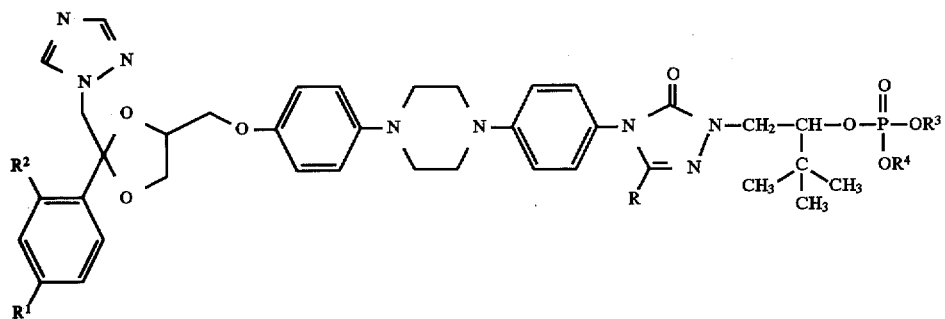

| Co. No. | Ex. No. | R | R¹ | R² | R³ | R⁴ | Physical data |
|---|---|---|---|---|---|---|---|
| | | | | | | | (c = 0.5% in DMF)/ |
| | | | | | | | (−)[(B-cis),A] |
| 22 | 15 | H | F | F | H | H | [(A-cis),A] |
| 23 | 16 | H | F | F | H | H | mp. 171.6° C./ |
| | | | | | | | $[\alpha]_D^{20} = +10.93°$ |
| | | | | | | | (c = 0.5% in DMF) |
| 24 | 16 | H | F | F | H | H | [(B-cis),A].H₂O |
| 25 | 16 | H | F | F | H | H | NH₄⁺/[(A-cis),B] |
| 26 | 16 | H | F | F | H | H | mp. 167.8° C./ |
| | | | | | | | $[\alpha]_D^{20} = +12.59°$ |
| | | | | | | | (c = 1% in DMF) |
| 27 | 15 | H | F | F | H | H | $[\alpha]_D^{20} = 3.70°$ |
| | | | | | | | (c = 0.5% in methanol) |

TABLE 4

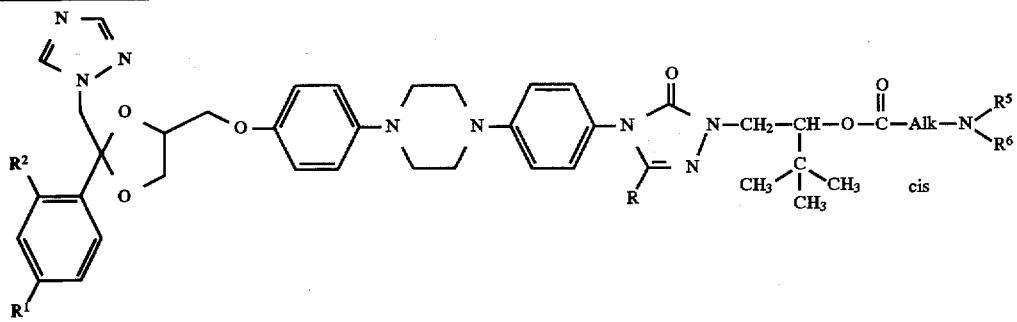

| Co. No. | Ex. No. | R | R¹ | R² | Alk | −N(R⁵)(R⁶) | Physical data |
|---|---|---|---|---|---|---|---|
| 28 | 18 | H | F | F | CH₂ | pyrrolidinyl | mp. 156.7° C. |
| 29 | 18 | H | F | F | CH₂ | 4-methylpiperazinyl | mp. 155.3° C. |
| 30 | 18 | H | F | F | CH₂ | −N(CH₂−CH₃)₂ | mp. 166.3° C. |
| 31 | 18 | H | F | F | CH₂ | 4-(2-hydroxyethyl)piperazinyl | mp. 171.7° C. .2HCl.H₂O |

TABLE 4-continued

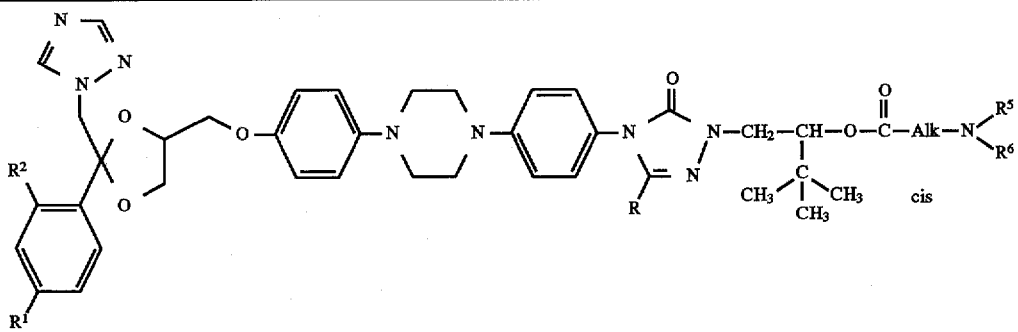

| Co. No. | Ex. No. | R | R¹ | R² | Alk | $-N\begin{smallmatrix}R^5\\R^6\end{smallmatrix}$ | Physical data |
|---|---|---|---|---|---|---|---|
| 32 | 19 | H | Cl | Cl | $CH_2$ | −N(piperazine)N−CH₃ | mp. 156.0° C. .2HCl.1/2H₂O |
| 33 | 19 | H | F | F | $CH_2-CH_2$ | −N(piperazine)N−CH₃ | mp. 213.7° C. .HCl |
| 34 | 19 | H | F | F | $CH_2$ | −N(piperazine)N−CH₃ | mp. 201.5° C. .HCl |
| 35 | 19 | H | F | F | $CH_2-CH_2$ | −NH−C(=O)−O−C(CH₃)₃ | — |
| 36 | 20 | H | F | F | $CH_2-CH_2$ | $NH_2$ | mp. 217.9° C. .HCl |
| 37 | 21 | H | F | F | $CH_2-CH_2$ | −N(pyrrolidine) | mp. 154.4° C. .HCl.H₂O |
| 38 | 21 | H | F | F | $CH_2$ | $NH_2$ | mp. 219.5° C. .HCl |
| 39 | 21 | H | F | F | $CH_2-CH_2$ | −N(piperazine)N−$(CH_2)_2$−OH | mp. 208.5° C. .2HCl |

C. Physicochemical Example

Example 22

Solubility

An excess of compound was added to 5 ml of solvent (the type of solvent is specified in the table). The mixture was shaken during 1 hour at room temperature. The precipitate was filtered off. The pH of the remaining solvent was measured and is shown in the table. The concentration of the compound was measured via UV-spectroscopy and is shown in the column "Solubility".

| Co. No. | Solvent | pH | Solubility (mg/ml) |
|---|---|---|---|
| 2 | water | 7.01 | >6 |
| 3 | water | 6.95 | 31.93 |
| 7 | water | 6.80 | 0.35 |
| 9 | water | 6.65 | 2.65 |
| 29 | 0.1N HCl | 1.62 | 4.89 |
| 30 | 0.1N HCl | 1.65 | 5.22 |
| 33 | 0.1N HCl | 1.65 | >6 |
| 34 | 0.1N HCl | 1.75 | >6 |
| 36 | 0.1N HCl | 1.25 | >6 |
| 37 | 0.1N HCl | 1.26 | >6 |
| 38 | 0.1N HCl | 1.59 | >6 |
| 31 | 0.1N HCl | 1.53 | >6 |

D. Pharmacological Examples

Example 23

Mouse Triple Mycosis Model

The test compounds were evaluated for their activity in a mouse model of fungal infection in which three mycoses—vaginal candidosis, cutaneous trichophytosis and disseminated aspergillosis—were established simultaneously. The mice, in groups of 10, were pretreated with subcutaneous injections of oestradiol valerate (500 µg) then inoculated on day 0 with the following: 100 000 colony forming units (CFU)/g of *Aspergillus fumigatus* B 19119 intravenously, a suspension containing $10^8$ *Candida albicans* cells intravaginally and a aqueous suspension of *Trichophyton quinckeanum* on lightly scarified dorsal skin. Treatment with the test compounds (orally or intravenously) was begun on the day of infection and continued for 5 days. All animals that died spontaneously and those that survived and were sacrificed on day 6, were sampled for the numbers of *Aspergillus fumigatus* CFU/g in kidney and spleen, for skin lesion scores (0=no visible lesion; 1=a few point lesions; 2=moderate lesions; 3=severe lesions) and for *Candida albicans* CFU from a vaginal swab.

Mouse Disseminated Candida Model

Mice in groups of 10 were infected intravenously with $8 \times 10^5$ CFU of *Candida albicans*. Treatment was begun on the day of infection and repeated daily for 9 days. *Candida albicans* CFU/g kidney were measured for all mice that died spontaneously or were killed on day 10.

The table indicates the lowest concentrations of the shown compounds that achieved a reduction in mean Candida counts of 1 log (i.e. a 10-fold reduction) or more, either in the triple mycosis model or the disseminated Candida infection; also the lowest concentrations that reduced mean skin scores below 1.0 in the cutaneous dermatophytosis component of this model (NT=nor tested, IV=intravenous).

| | Mouse triple mycosis model | | | | Mouse disseminated |
|---|---|---|---|---|---|
| | Vaginal Candida CFU reduced by 1 log or more | | Dermatophyte skin score reduced to ≤1 | | Candida model Kidney Candida CFU reduced by 1 log or more |
| CN | IV route | oral route | IV route | oral route | IV route |
| 34 | 2.5 | 2.5 | 2.5 | 2.5 | 5 |
| 3 | 2.5 | 2.5 | 2.5 | 2.5 | 10 |
| 17 | <2.5 | NT | <2.5 | NT | NT |

Example 24

Determination of Fungal Susceptibility

A panel of Candida isolates plus single isolates of the dermatophytes *Microsporum canis*, *Trichophyton rubrum* and *T. mentagrophytes; Aspergillus fumigates*, and *Cryptococcus neoformans* were used to evaluate the activity of the test compounds in vitro. Inocula were prepared as broth cultures (yeasts) or as suspensions of fungal material made from agar slope cultures (moulds). The test compounds were pipetted from DMSO stock solution into water to provide a series of 10-fold dilutions. The fungal inocula were suspended in the growth medium CYG (F.C. Odds, Journal of Clinical Microbiology, 29, (2735–2740, 1991) at approximately 50000 colony-forming units (CFU) per ml and added to the aqueous test drugs.

The cultures were set up in the 96 wells of plastic microdilution plates and they were incubated for 2 days at 37° C. (*Candida spp.*) or for 5 days at 30° C. (other fungi). Growth in the microcultures was measured by its optical density (OD) measured at a wavelength of 405 nm. The OD for cultures with test compounds was calculated as a percentage of the control, drug-free OD. Inhibition of growth to 35% of control or less was recorded as significant inhibition.

Minimal inhibitory concentration (MICs) of intermediates 15, 16, 17, 18, 24 range from ≤0.01 to about 10 µM *Candida glabrata, Candida krusei, Candida parapsilosis*, nonazole-resistent *Candida albicans, Candida kefyr, Microsporum canis, Trichophyton rubrum, Trichophyton mentagrophytes, Cryptococcus neoformans, Aspergillus fumigatus*.

E. Composition Examples

"Active ingredient" (A.I.) as used throughout these examples relates to a compound of formula (I), a pharmaceutically acceptable acid addition salt or a stereochemically isomeric form thereof.

Example 25

Oral Drops

500 Grams of the A.I. was dissolved in 0.5 l of a sodium hydroxide solution and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

Example 26

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

Example 27

Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3- propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example 28

Injectable Solution 1.8 Grams methyl 4-hydroxybenzoate and 0.2 grams sodium hydroxide were dissolved in about 0.5 l of boiling water for injection. After cooling to about 50° C. there were added while stirring 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

Example 29

Suppositories

3 Grams A.I. was dissolved in a solution of 3 grams 2,3-dihydroxybutanedioic acid in 25 ml polyethylene glycol 400. 12 Grams surfactant (SPAN®) and triglycerides (Witepsol 555®) q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

We claim:

1. A compound of formula (I),

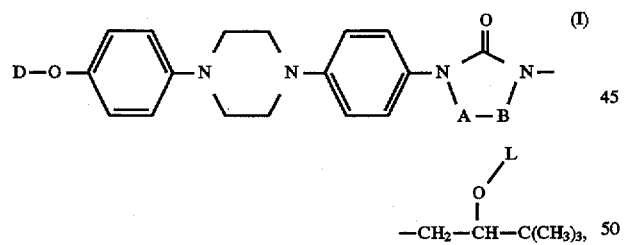

a pharmaceutically acceptable acid or base addition salt thereof or a stereochemically isomeric form thereof, wherein A and B taken together form a bivalent radical of formula:
—N=CH— (a),
—CH=N— (b),
—CH$_2$—CH$_2$— (c),
—CH=CH— (d),
—C(=O)—CH$_2$— (e),
—CH$_2$—C(=O)— (f), wherein one hydrogen atom in the radicals (a) and (b) may be replaced with a $C_{1-6}$-alkyl-radical and up to two hydrogen atoms in radical (c), (d), (e) or (f) may be replaced by a $C_{1-6}$-alkyl-radical;

D is a radical of formula

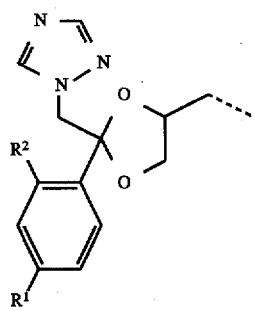

(D$_1$)

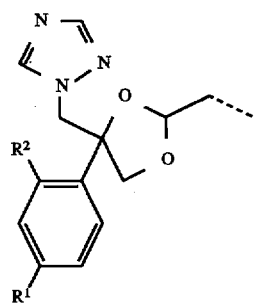

(D$_2$)

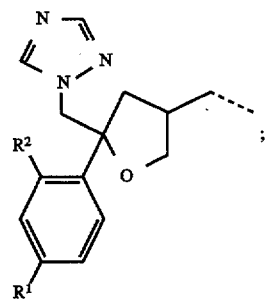

(D$_3$)

L is a radical of formula

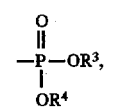

(L$_1$)

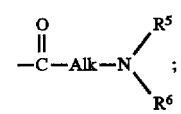

(L$_2$)

Alk is a $C_{1-4}$alkanediyl radical;
$R^1$ is halo;
$R^2$ is hydrogen or halo;
$R^3$ is hydrogen, $C_{1-6}$alkyl, phenyl or halophenyl;
$R^4$ is hydrogen, $C_{1-6}$alkyl, phenyl or halophenyl;
$R^5$ is hydrogen or $C_{1-6}$alkyl;
$R^6$ is hydrogen, $C_{1-6}$alkyl, $C_{1-6}$alkyloxycarbonyl, or
$R^5$ and $R^6$ taken together with the nitrogen atom to which they are attached form a pyrrolidine, piperidine, morpholine, piperazine or substituted piperazine ring, said substituted piperazine being a piperazine ring substituted on the 4-position of the piperazine ring with $C_{1-6}$alkyl, hydroxy$C_{1-6}$alkyl, amino$C_{1-6}$alkyl, mono- or di($C_{1-6}$alkyl) amino$C_{1-6}$alkyl.

2. A compound according to claim 1, wherein D is a radical of formula (D$_1$) or (D$_2$).

3. A compound according to claim 2, wherein D is a radical of formula (D$_1$), wherein $R^1$ is chloro or fluoro and $R^2$ is hydrogen, chloro or fluoro; L is a radical of formula ($L_1$), wherein $R^3$ and $R^4$ each independently are phenyl or hydrogen.

4. A compound according to claim 3, wherein the compound is (±)-cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2-[3,3-dimethyl-2-(phosphonooxy)butyl]-2,4-dihydro-3H-1,2,4-triazol-3-one, a stereochemically isomeric form or a base addition salt form thereof.

5. A composition comprising a pharmaceutically acceptable carrier and as active ingredient an antifungally effective amount of a compound as claimed in claim 1.

6. A composition comprising a pharmaceutically acceptable carrier and as active ingredient an antifungally effective amount of a compound as claimed in claim 2.

7. A composition comprising a pharmaceutically acceptable carrier and as active ingredient an antifungally effective amount of a compound as claimed in claim 3.

8. A composition comprising a pharmaceutically acceptable carrier and as active ingredient an antifungally effective amount of a compound as claimed in claim 4.

9. A method of inhibiting the development of or eliminating fungi in warm blooded animals suffering from infection by said fungi, which method comprises administering to said warm blooded animals an antifungally effective amount of a compound as claimed in claim 1.

10. A method of inhibiting the development of or eliminating fungi in warm blooded animals suffering from infection by said fungi, which method comprises administering to said warm blooded animals an antifungally effective amount of a compound as claimed in claim 2.

11. A method of inhibiting the development of or eliminating fungi in warm blooded animals suffering from infection by said fungi, which method comprises administering to said warm blooded animals an antifungally effective amount of a compound as claimed in claim 3.

12. A method of inhibiting the development of or eliminating fungi in warm blooded animals suffering from infection by said fungi, which method comprises administering to said warm blooded animals an antifungally effective amount of a compound as claimed in claim 4.

* * * * *